(12) United States Patent
Weyl et al.

(10) Patent No.: US 7,191,640 B2
(45) Date of Patent: Mar. 20, 2007

(54) GAS SENSOR

(75) Inventors: Helmut Weyl, Schwieberdingen (DE); Juergen Wilde, Fellbach (DE); Dirk Bluemmel, Schwieberdingen (DE); Andreas Pesch, Krefeld (DE)

(73) Assignee: Robert Bosh GmbH, Stuttgart (DE)

( * ) Notice: Subject to any disclaimer, the term of this patent is extended or adjusted under 35 U.S.C. 154(b) by 365 days.

(21) Appl. No.: 10/363,729

(22) PCT Filed: Jul. 4, 2002

(86) PCT No.: PCT/DE02/02440

§ 371 (c)(1),
(2), (4) Date: Jul. 28, 2003

(87) PCT Pub. No.: WO03/005009

PCT Pub. Date: Jan. 16, 2003

(65) Prior Publication Data

US 2004/0025565 A1 Feb. 12, 2004

(30) Foreign Application Priority Data

Jul. 6, 2001 (DE) .............................. 101 32 826

(51) Int. Cl.
*G01N 7/00* (2006.01)
(52) U.S. Cl. ............... 73/31.05; 73/31.05; 73/23.31; 73/28.01

(58) Field of Classification Search ............ 73/31.05, 73/23.31, 28.01
See application file for complete search history.

(56) References Cited

U.S. PATENT DOCUMENTS

| 5,246,562 | A | * | 9/1993 | Weyl et al. | .................. | 204/424 |
| 6,082,175 | A | * | 7/2000 | Yoshikawa et al. | ........ | 73/23.31 |
| 2002/0148280 | A1 | * | 10/2002 | Weyl et al. | ................ | 73/31.05 |

FOREIGN PATENT DOCUMENTS

| DE | 198 27 542 | 12/1999 |
| DE | 198 33 861 | 2/2000 |
| EP | 0 506 897 | 12/1995 |
| WO | WO 92/08127 | 5/1992 |
| WO | WO 01/96850 | 12/2001 |

OTHER PUBLICATIONS

International Search Report dated Mar. 3, 2003 from PCT International Patent Application No. PCT/DE02/02440.

* cited by examiner

*Primary Examiner*—Hezron Williams
*Assistant Examiner*—André K. Jackson
(74) *Attorney, Agent, or Firm*—Kenyon & Kenyon

(57) ABSTRACT

Electrical connecting lines of a sensor element are anchored by friction locking, specifically using an annularly closed spring element which clamps the connecting lines against contact surfaces on the sensor element using pressure bodies.

16 Claims, 6 Drawing Sheets

GAS SENSOR

FIELD OF THE INVENTION

The present invention relates to a gas sensor for monitoring a parameter of a gas component, a lambda sensor in particular, including a sensor element, a contact surface arranged on the outside as well as a connecting line connected to it electrically, the connecting line being clamped by friction locking between the contact surface and a pressure body using a spring element surrounding the sensor element, the spring element holding the pressure body against the sensor element.

BACKGROUND INFORMATION

The electrodes of a lambda sensor or of another such gas sensor are electrically connected to connecting lines, across which the electrodes are electrically connected to the input side of an electronic evaluation circuit or an electronic engine management system of an internal combustion engine, to which the gas sensor or the lambda sensor is assigned. Clamp connections are often preferred between the connecting lines and the contact surfaces arranged on the sensor element, as is referred to in, for example, European Patent No. 0 506 897.

When placed in an exhaust line of an internal combustion engine, gas sensors or lambda sensors are exposed to extraordinarily high temperatures of up to 1200° C. For that reason, the spring elements maintaining the friction-locked connection is configured to be insensitive to temperature.

SUMMARY OF THE INVENTION

According to the present invention, it is provided that the spring element is annularly closed and is positioned with initial tension, which is preserved even with a severe increase in temperature.

The annularly closed configuration may allow very high initial tensions so that adequate clamping forces are still present even at high temperatures.

According to a first exemplary embodiment, the spring element may be configured as a sleeve-like ring, which presses the pressure bodies against the sensor element in the manner of a clamping ring, the spring element being shrunk onto the pressure bodies and/or is slid onto a conical section formed by the pressure bodies with great force. An interference fit capable of bearing high loads is formed in this manner.

According to another exemplary embodiment of the present invention, the spring element includes at least one spring section, which in the clamped state is deformed in alignment with an component parallel to the longitudinal axis of the sensor element. This exemplary embodiment may allow contact to the sensor element in a simple manner and simple assembly.

Another exemplary embodiment includes two approximately diametrically opposed first spring sections as well as at least two additional diametrically opposed spring sections, the first spring sections defining an arched virtual plane relative to a radial axis of the annular spring element and the additional spring sections being between the first spring sections on or in front of the convex side of the arched surface.

A large effective spring length is attained with this spring element, torsion being applied to the transitional areas between the first and the additional spring sections with the consequence that the spring characteristic is comparatively flat and a readily reproducible clamping force is ensured. Moreover, temperature fluctuations have only a slight influence on the clamping force because it is allowed to the greatest possible extent to compensate an elongation of the first spring sections by an elongation of the additional spring sections.

The annularly closed spring elements are configured in such a manner that they apply force to the pressure bodies with areas (tongues) directed radially inward. With such a configuration of the spring elements, opposing size changes occur at the spring element when the temperature is increased due to an expansion of the outer diameter of the spring element and the radial length of the areas directed radially inward.

Such spring elements may be configured as stampings.

The pressure bodies are configured in such a manner that the tension of the spring element is inevitably increased when the spring element is moved on the pressure bodies from one axial end of the pressure bodies in the direction of the other axial ends.

An exemplary embodiment of the present invention may provide that the pressure bodies are already held together under spring tension when the spring element is slid onto the one axial end.

In addition, the mutually facing sides of the pressure bodies in this position of the spring element may form a mouth open at the other axial ends of the pressure bodies for inserting the sensor element, which is then held securely with great force between the pressure bodies when the spring element is slid to the other axial ends of the pressure bodies.

DETAILED DESCRIPTION

Figure 1:
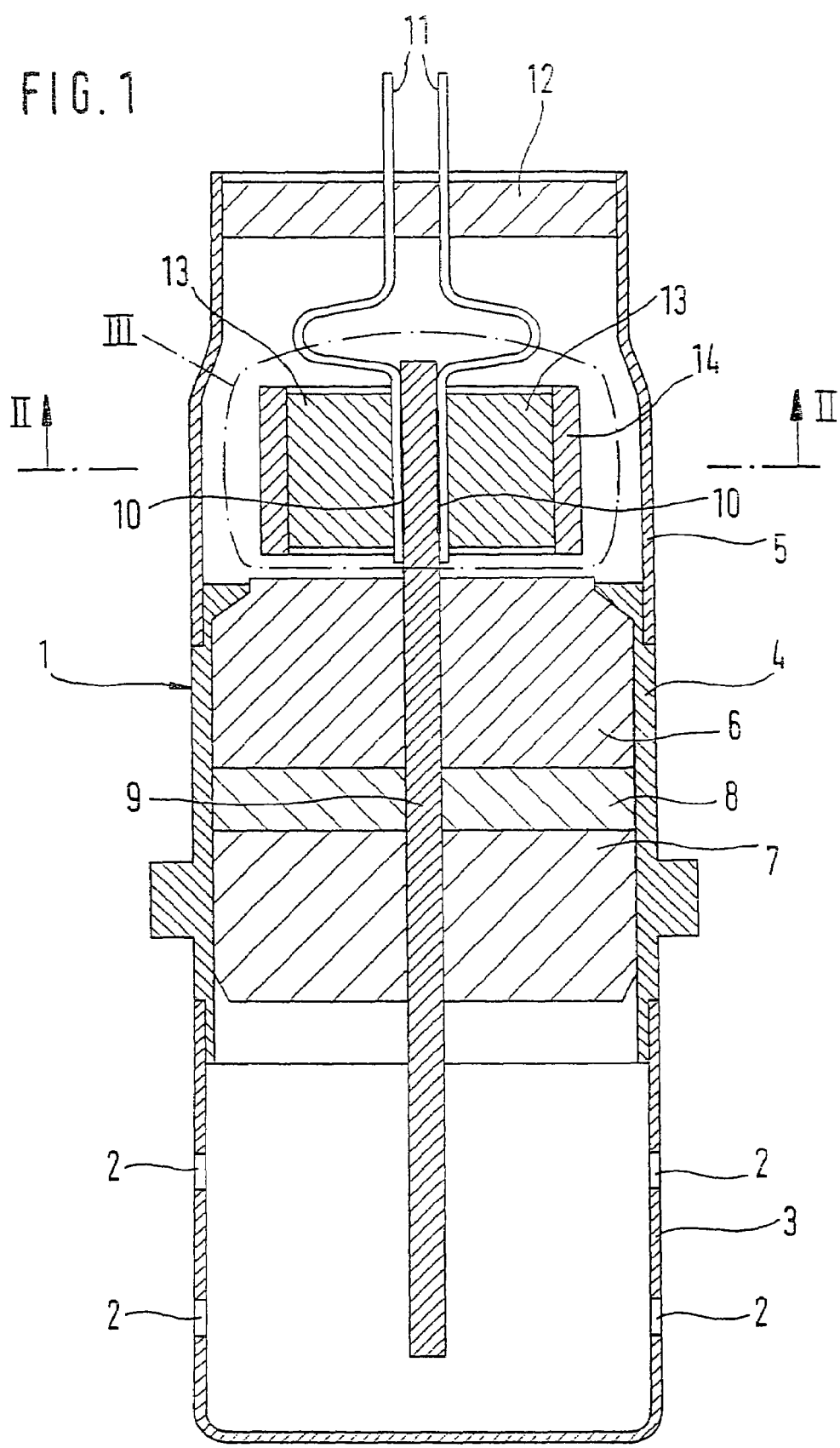
FIG. 1 shows a longitudinal section of a gas sensor according to the present invention.

A longitudinal section of a gas sensor 1 is shown in diagrammatic form in FIG. 1. The gas sensor includes a housing which is made up of a protective tube 3 provided with openings 2 on the side of the gas to be analyzed, a center sleeve part 4, and a tube part 5. These parts are securely joined together, for example, by welding.

Two molded ceramic parts 6 and 7 are arranged within sleeve part 4, a ceramic sealing element 8 being accommodated between them, the ceramic sealing element preventing gas from penetrating from the interior of protective tube 3 to the interior of tube part 5. Molded ceramic parts 6 and 7 hold a ceramic sensor element 9 penetrating sealing element 8 and molded ceramic parts 6 and 7, the lower end of ceramic sensor element 9, as seen in FIG. 1, being configured as a lambda sensor in a manner known per se, the electrodes of which being electrically connected to contact surfaces 10 arranged at the other end of the body of sensor element 9 via electrical printed conductors, which are not shown, accommodated in sensor element 9.

These contact surfaces 10 are electrically connected to connecting lines 11, which penetrate sealing disk 12 made of an electrically insulating material which seals the upper end of tube part 5, and are secured by embedding in sealing disk 12.

Figure 2:
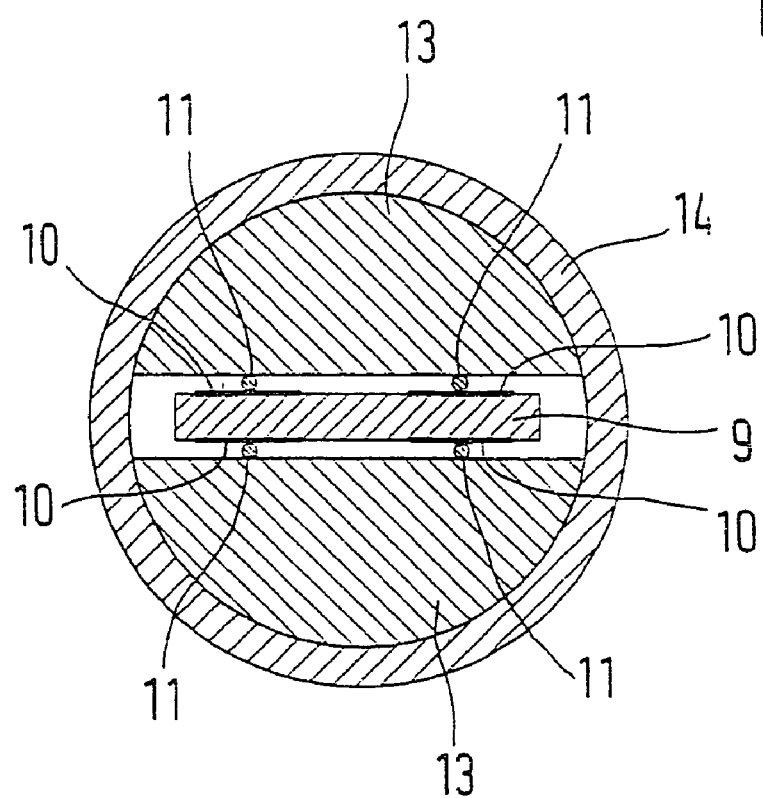
FIG. 2 shows a sectional drawing corresponding to section line II—II in FIG. 1.

The electrical contact between contact surfaces 10 and connecting lines 11 is maintained due to the fact that connecting lines 11 are pressed against contact surfaces 10 by ceramic pressure bodies 13. To this end, pressure bodies 13, which according to FIG. 2 together have an approximately circular cross-section, are arranged within a spring element 14 configured as a clamping ring which encloses pressure bodies 13 with high initial tension and clamps them against the facing sides of sensor element 9. Accordingly, connecting lines 11 are held securely by friction locking between one pressure body 13 each and assigned contact surface 10 in electrical connection with the particular contact surface 10.

In addition, connecting lines 11 may be glued to sensor element 9 and/or welded to the particular contact surfaces 10.

According to an exemplary embodiment of the present invention, clamping ring-like spring element 14 may be shrunk onto pressure bodies 13. To that end, spring element 14 is produced with an undersize relative to the cross-section of pressure bodies 13 and sensor element 9 connected between them and it is expanded by intense heat utilizing the associated thermal expansion of the steel material forming spring element 14 so that spring element 14 may be slid axially onto pressure bodies 13 after sensor element 9 and connecting lines 11 between pressure bodies 13 have been interconnected.

Figure 3:
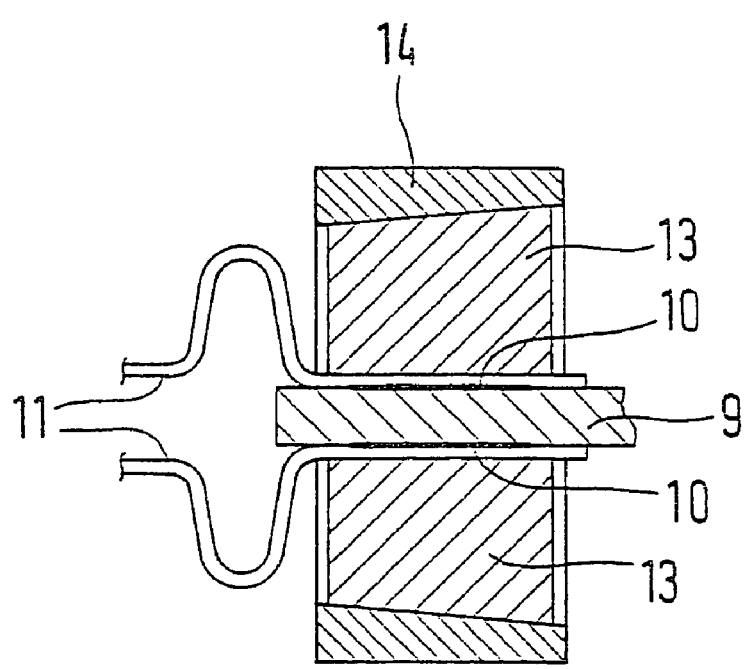
FIG. 3 shows another embodiment of detail III in FIG. 1.

Instead, the outer circumference of pressure bodies 13 according to FIG. 3 may be formed as a cone and to form the inner circumference of clamping ring-like spring element 14 correspondingly as an inner cone, such that spring element 14 may be slid onto pressure bodies 13 with increasing tension and to anchor it thereon by self-retention.

Figure 4:
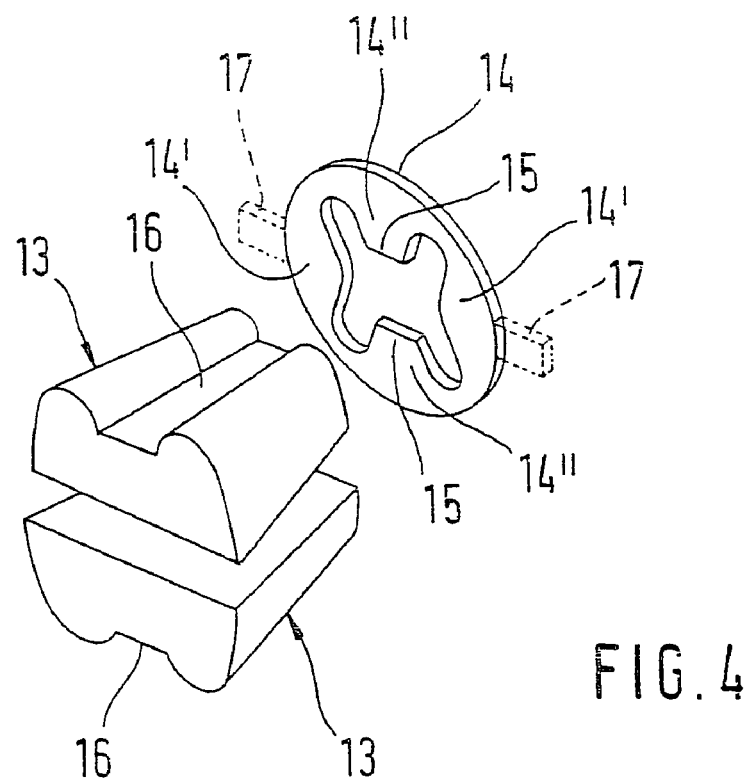
FIG. 4 shows a representation of a spring element in perspective with assigned pressure bodies.
Figure 5:
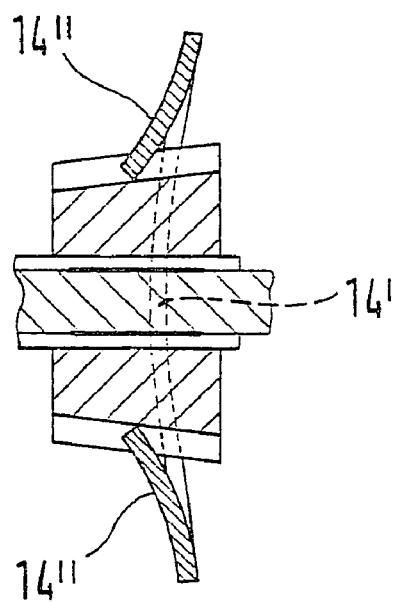
FIG. 5 shows a representation of a system corresponding to FIG. 3 including a spring element and pressure bodies according to FIG. 4.

In the exemplary embodiment of FIGS. 4 and 5, spring element 14 is an annular closed stamped disk part including an H-shaped opening in cross-section in such a manner that tabs 15 directed inward are formed on the disk-shaped spring element. These tabs 15 engage in axial channels 16 formed on the outsides of pressure bodies 13. The bottoms of channels 16 may be configured as inclined ramps which rise from the left ends of pressure bodies 13 in FIG. 5 in the direction of their right ends.

When disk-shaped spring element 14 according to FIG. 5 is increasingly slid axially onto pressure bodies 13 in the direction of the ascending gradient of the aforementioned ramps, tabs 15 are bent away against the direction of sliding. At the same time, disk-shaped spring element 14 is arched, the concave side of the arched disk pointing in the direction of sliding. As a result, the areas of disk-shaped spring element 14 connecting tabs 15 form first spring sections 14' while tabs 15 form additional spring sections 14", torsion being applied to the disk areas between spring sections 14' and 14". The free ends of tabs 15 seated on the bottoms of channels 16 are arranged in front of the convex side of the arch formed by disk-shaped spring element 14.

With appropriate dimensioning of tabs 15 and the thickness of disk-shaped spring element 14, which in turn is produced from a spring steel material, e.g., Inconell, pressure bodies 13 are pressed against sensor element 9 with high pressure forces so that connecting lines 11 are in turn held securely on assigned contact surfaces 10 by friction locking, see FIG. 5.

If necessary, the pressure forces may be increased by sliding multiple disk-shaped spring elements 14 onto pressure bodies 13.

Radial extensions 17 may be provided on the outer circumference of disk-shaped spring element 14, the radial extensions being positioned transversely to tabs 15 and being able to brace spring element 14 by bending elastically at the internal circumferential wall of tube part 5 (see FIG. 1). This ensures an additional anchoring of spring element 14 to tube part 5 of the housing of gas sensor 1 as well as vibration damping for the parts clamped in place by spring element 14—pressure body 13, sensor element 9, and connecting lines 11.

Figure 6:
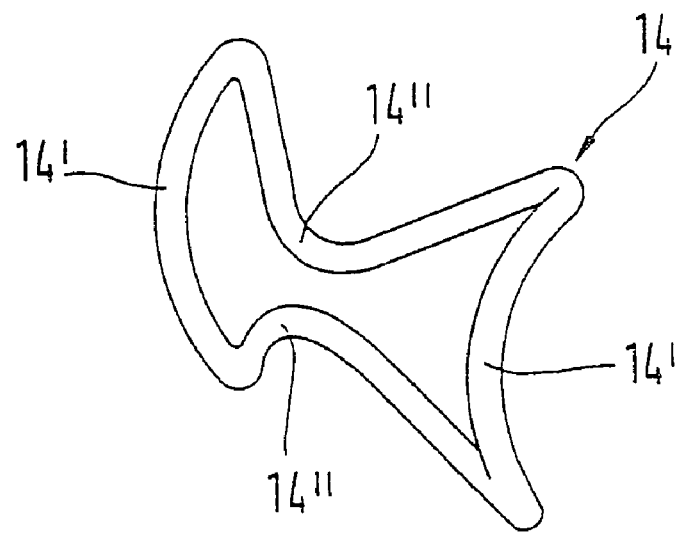
FIG. 6 shows another embodiment of the spring element.

Spring element 14 shown in FIG. 6 is configured as an annularly wire closed strap part with first spring sections 14' and second spring sections 14", first spring sections 14' again defining an arched plane and the areas of second spring sections 14" seated on pressure bodies 13 lying in front of the convex side of the arched plane.

Figure 7:
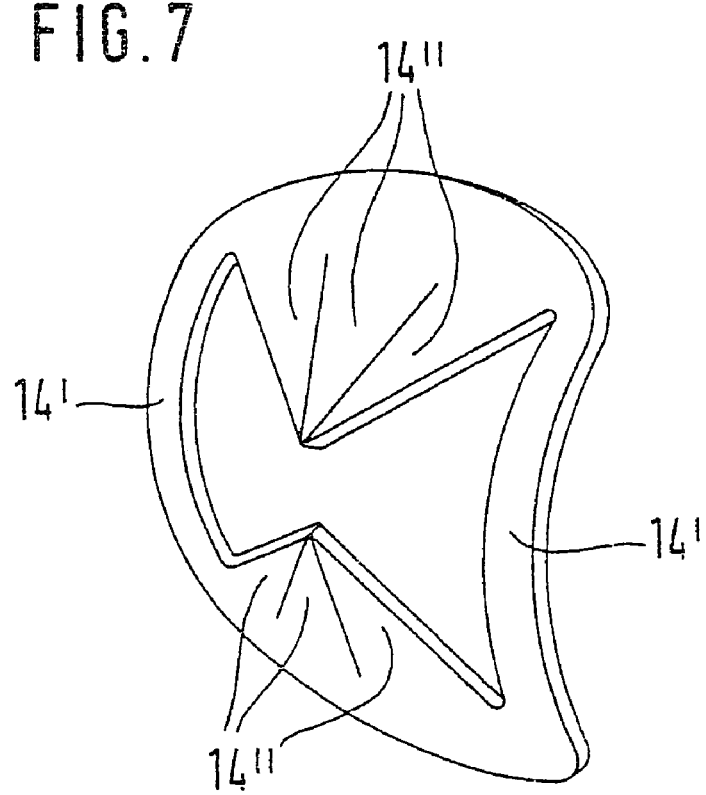
FIG. 7 shows another embodiment of the spring element.

FIG. 7 shows another exemplary embodiment, first spring sections 14' again being configured as wire straps and second spring sections 14" being configured in the form of bending tongues, the free ends of which are seated under tension on particular pressure bodies 13.

Figure 8:
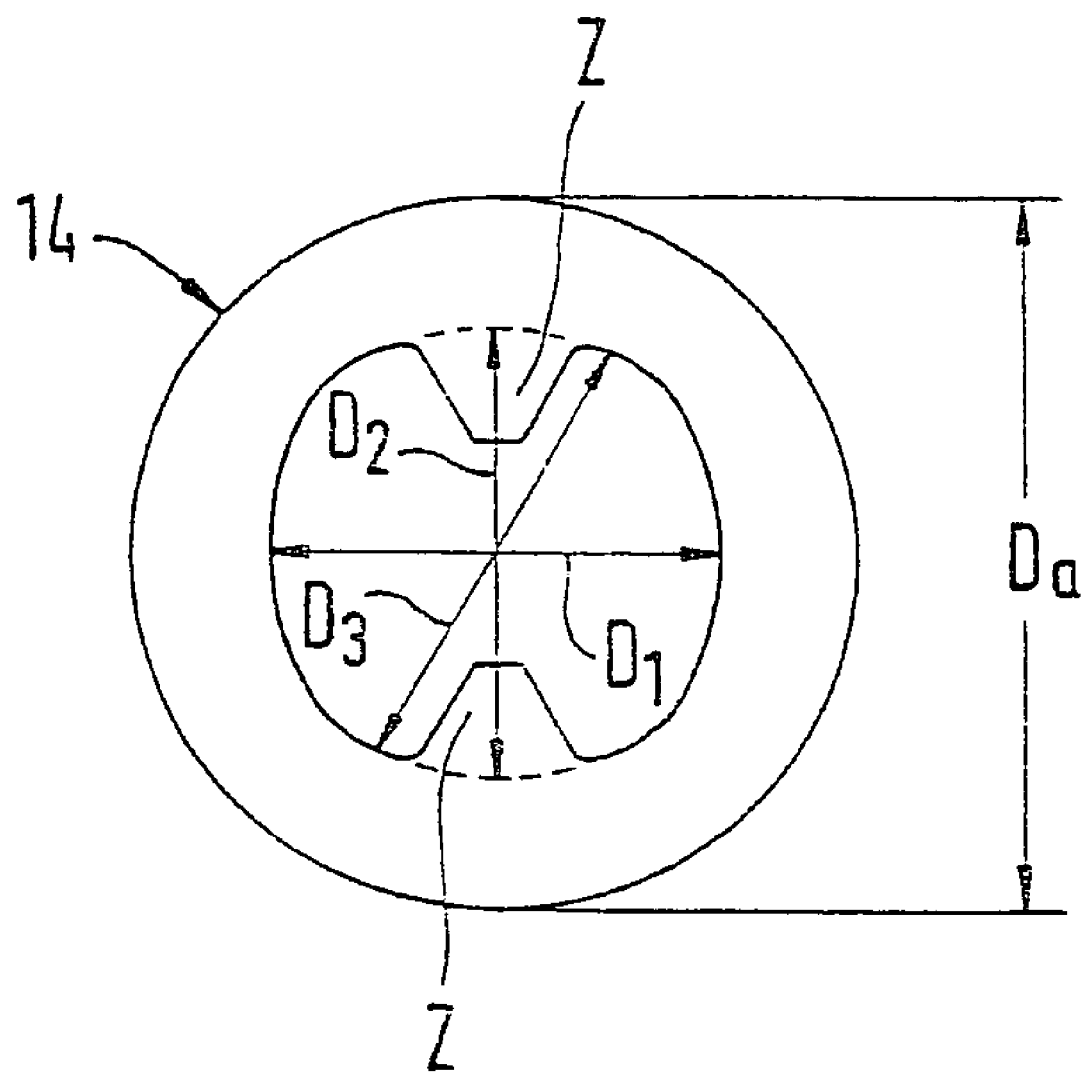
FIG. 8 shows a spring element.

Spring element 14 of FIG. 8 is configured as a circular disk-shaped stamping from spring steel plate. It has a thickness of, e.g., 4 to 7 mm and a circular outer circumference with an outer diameter $D_a$ of 10.2 mm, for example. Formed on the inner circumference are two trapezoidal tongues Z, with which spring element 14 clamps the pressure bodies, described below with reference to FIGS. 9 through 14, against one another. Moreover, the inner circumference of spring element 14 is formed out-of-round, it being possible, for example, for one internal diameter $D_1$ to have a size of 6 mm, an internal diameter $D_2$ a size of 6.4 mm, and an internal diameter $D_3$ a size of 6.6 mm. The varying radial width of spring element 14 takes into account the locally varying bending forces and torsion forces that occur at the spring element when it is used according to specifications to clamp the pressure bodies against the sensor element. In the form shown, the load on the spring material is roughly equal everywhere. An approximately linear increase in force is attained in particular when the facing ends of tongues Z are pressed apart.

Spring element 14 of FIG. 8 interacts with pressure bodies 13 in the manner shown in FIGS. 9 through 14. This pressure body is used pair-wise, by analogy to pressure bodies 13 in FIGS. 4 and 5. Tongues Z of spring element 14 shown in FIG. 8 correspond to spring sections 14" of spring element 14 in FIGS. 4 through 7.

Figure 10:
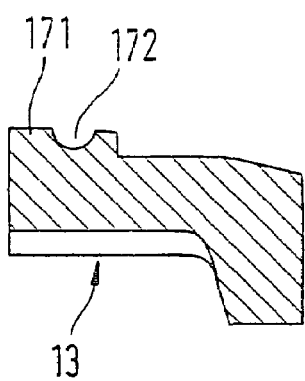
FIG. 10 shows sectional drawings corresponding to section lines X—X in FIG. 9 and XII—XII in FIG. 11.
Figure 9:
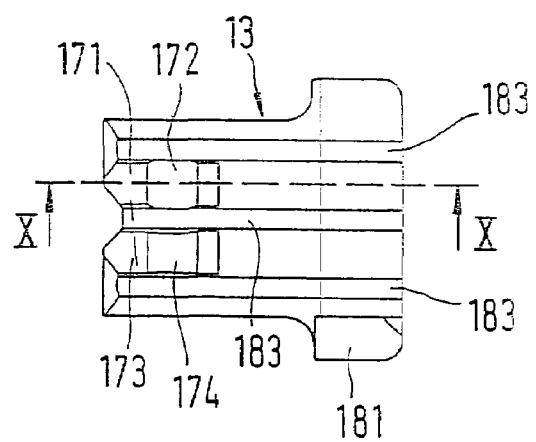
FIG. 9 shows the pressure body side facing the sensor element of FIG. 8 to be anchored.
Figure 13:
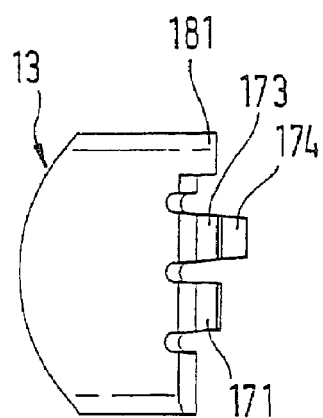
FIG. 13 shows the two end faces of the pressure body.
Figure 11:
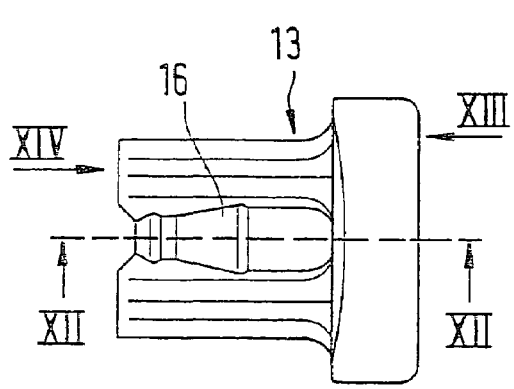
FIG. 11 shows the opposite side of a pressure body.
Figure 14:
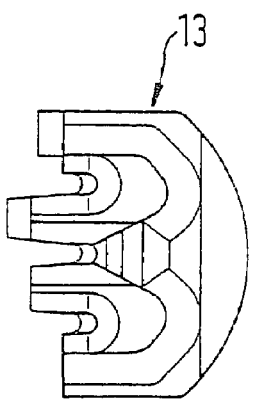
FIG. 14 shows the two end faces of the pressure body.

FIG. 9 shows the side facing the sensor element (not shown) to be anchored. The opposite side of pressure body 13 is shown in FIG. 11. FIGS. 13 and 14 show the two end faces of the pressure body and FIGS. 10 and 12 show sectional drawings corresponding to section lines X—X in FIG. 9 and XII—XII in FIG. 11.

Figure 12:
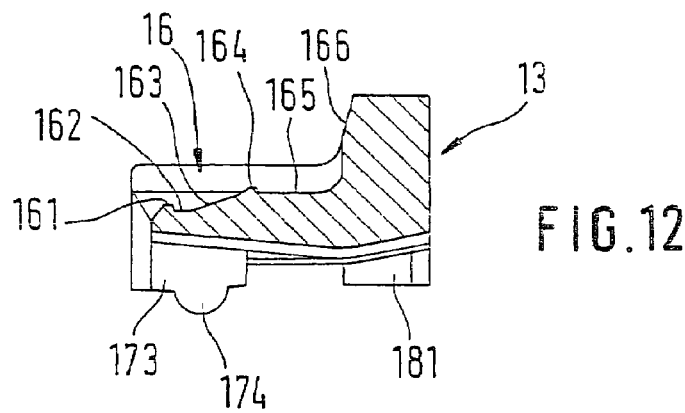
FIG. 12 shows sectional drawings corresponding to section lines X—X in FIG. 9 and XII—XII in FIG. 11.

As is apparent from FIGS. 11 and 12 in particular, pressure body 13 includes an outside axial channel 16, which is engaged by one of tongues Z of the spring element of FIG. 8. At the left end of pressure body 13 in FIGS. 11 and 12, the bottom of channel 16 includes a first notch elevation 161, which is adjoined to the right by a first notch surface 162. To the right, this first notch surface changes into a ramp 163, which is adjoined by an additional notch elevation 164 and an additional notch surface 165 located behind it.

When tongues Z of spring element 14 of FIG. 8 are pushed over first notch elevation 161 to first notch surface 162, spring element 14 occupies a first notch position. If spring element 14 is pushed further to the right in FIGS. 11 and 12—with increasing bending of the tongues and entire spring element 14—tongues Z are brought across ramp 163 and additional notch elevation 164 into a strongly tensioned notch position in which the tongues are clamped against additional notch surface 165 and the annular disk-shaped spring element is in contact with a stop surface 166 of pressure body 13 with osculation.

A special feature of pressure body 13 shown in FIGS. 9 through 14 is that, together with a similar pressure body, it forms a mouth suitable for accommodating sensor element 9 (see FIG. 1), it being possible to hold sensor element 9 with it in a manner similar to pliers.

To this end, the left end of pressure body 13 according to FIGS. 9, 10, and 12 includes a projection 171 including in cross-section an approximately semicircular recess 172 and an additional projection 173 including an elevation 174 diametrically opposed to recess 172.

If pressure bodies 13 shown in FIGS. 9 through 14 are arranged in pairs, recess 172 of one pressure body accommodates elevation 174 of the other pressure body and vice versa. Projections 171 and 173 with their recesses 172 and elevations 174 thus form a "mandibular joint" which is held together by spring element 14 of FIG. 8 when its tongues Z are seated on first notch surfaces 162.

A lateral projection 181 is arranged at the right end of the pressure body in FIGS. 9 and 12 and is also visible in the views of FIGS. 13 and 14. If two pressure bodies 13 of the type shown in FIGS. 9 through 14 are arranged in pairs forming the aforementioned mandibular joint, lateral projection 181 of each pressure body is aligned with a diametrically opposed flat area without a projection on the other pressure body 13.

Between the facing sides (see FIG. 9) of the two pressure bodies 13, a sensor element may be slid into the area between lateral projections 181 of the two pressure bodies 13 after the connecting wires to be contacted have been inserted or pushed into axial grooves 183, see FIG. 9.

Once spring element 14 of FIG. 8 has been pushed against stop surface 166, the mouth formed between pressure bodies 13 and accommodating the sensor element is closed with great force so that the connecting wires are pressed against the corresponding contact surfaces.

What is claimed is:

1. A gas sensor for monitoring a parameter of a gas component, the gas sensor comprising:
    a sensor element;
    at least one contact surface arranged on the sensor element;
    at least one pressure body held against the sensor element by a spring element that includes at least one spring section, which, in a clamped state, is deformed in alignment with a component in parallel with a longitudinal axis of the sensor element; and
    a connecting line connected electrically to the at least one contact surface, the connecting line being clamped by friction locking between the contact surface and the at least one pressure body;
    wherein the gas sensor is one of a lambda sensor and a temperature sensor; and
    wherein the at least one spring section includes a tongue-like area directed radially inwardly and which engages in an axial channel of the at least one pressure body, the at least one spring section being elastically deformed in the clamped state.

2. A gas sensor for monitoring a parameter of a gas component, the gas sensor comprising:
    a sensor element;
    at least one contact surface arranged on the sensor element;
    at least one pressure body held against the sensor element by a spring element that includes at least one spring section, which, in a clamped state, is deformed in alignment with a component in parallel with a longitudinal axis of the sensor element; and
    a connecting line connected electrically to the at least one contact surface, the connecting line being clamped by friction locking between the contact surface and the at least one pressure body;
    wherein the gas sensor is one of a lambda sensor and a temperature sensor; and
    wherein the spring element is annularly closed, and in a tensioned state, includes two approximately diametrically opposed first spring sections and at least two additional spring sections, the first spring sections defining an arched virtual plane relative to a radial axis of the spring element, and the at least two additional spring sections being between the first spring sections one of on and in front of a convex side of the arched virtual plane.

3. A gas sensor for monitoring a parameter of a gas component, the gas sensor comprising:
    a sensor element;
    at least one contact surface arranged on the sensor element;
    at least one pressure body held against the sensor element by a spring element that includes at least one spring section, which, in a clamped state, is deformed in alignment with a component in parallel with a longitudinal axis of the sensor element; and
    a connecting line connected electrically to the at least one contact surface, the connecting line being clamped by friction locking between the contact surface and the at least one pressure body;
    wherein the gas sensor is one of a lambda sensor and a temperature sensor; and
    wherein the at least one spring section includes a spring strap.

4. The gas sensor of claim 2, wherein the at least two additional spring sections includes tongue-like parts.

5. A gas sensor for monitoring a parameter of a gas component, the gas sensor comprising:
    a sensor element;
    at least one contact surface arranged on the sensor element;
    at least one pressure body held against the sensor element by a spring element, wherein the spring element is annularly closed and is one of a clamping ring and a clamping sleeve that is shrunk onto the at least one pressure body; and a connecting line connected electrically to the at least one contact surface, wherein the connecting line is clamped by friction locking between the at least one contact surface and the at least one pressure body;

wherein the gas sensor is one of a lambda sensor and a temperature sensor; and wherein the spring element includes a spring ring in a washer shape, including areas of varying radial width.

6. A gas sensor for monitoring a parameter of a gas component, the gas sensor comprising:

a sensor element;

at least one contact surface arranged on the sensor element;

at least one pressure body held against the sensor element by a spring element that is annularly closed; and a connecting line connected electrically to the at least one contact surface, the connecting line being clamped by friction locking between the contact surface and the at least one pressure body;

wherein the gas sensor is one of a lambda sensor and a temperature sensor, the at least one pressure body is formed in a shape of a cone at least in an area, and the spring element is slidable axially onto the cone with tension by applying a torque bias; and wherein the spring element includes a spring ring in a washer shape, including areas of varying radial width.

7. A gas sensor for monitoring a parameter of a gas component, the gas sensor comprising:

a sensor element;

at least one contact surface arranged on the sensor element;

at least one pressure body held against the sensor element by a spring element that includes at least one spring section, which, in a clamped state, is deformed in alignment with a component in parallel with a longitudinal axis of the sensor element; and a connecting line connected electrically to the at least one contact surface, the connecting line being clamped by friction locking between the contact surface and the at least one pressure body;

wherein the gas sensor is one of a lambda sensor and a temperature sensor; and wherein the spring element includes a spring ring in a washer shape, including areas of varying radial width.

8. A gas sensor for monitoring a parameter of a gas component, the gas sensor comprising:

a sensor element;

at least one contact surface arranged on the sensor element;

at least one pressure body held against the sensor element by a spring element that includes at least one spring section, which, in a clamped state, is deformed in alignment with a component in parallel with a longitudinal axis of the sensor element; and a connecting line connected electrically to the at least one contact surface, the connecting line being clamped by friction locking between the contact surface and the at least one pressure body;

wherein the gas sensor is one of a lambda sensor and a temperature sensor; and wherein the spring element includes a stamped part.

9. A gas sensor for monitoring a parameter of a gas component, the gas sensor comprising:

a sensor element;

at least one contact surface arranged on the sensor element;

at least one pressure body held against the sensor element by a spring element, wherein the spring element is annularly closed and is one of a clamping ring and a clamping sleeve that is shrunk onto the at least one pressure body; and a connecting line connected electrically to the at least one contact surface, wherein the connecting line is clamped by friction locking between the at least one contact surface and the at least one pressure body;

wherein the gas sensor is one of a lambda sensor and a temperature sensor;

wherein the spring element clamps at least two pressure bodies against the sensor element, the at least two pressure bodies being approximately diametrically opposed relative to the sensor element; and wherein each of the at least two pressure bodies anchors at least one connecting line on an assigned contact surface of the sensor element through a frictionally locked connection produced by the spring element.

10. A gas sensor for monitoring a parameter of a gas component, the gas sensor comprising:

a sensor element;

at least one contact surface arranged on the sensor element;

at least one pressure body held against the sensor element by a spring element, wherein the spring element is annularly closed and is one of a clamping ring and a clamping sleeve that is shrunk onto the at least one pressure body; and a connecting line connected electrically to the at least one contact surface, wherein the connecting line is clamped by friction locking between the at least one contact surface and the at least one pressure body;

wherein the gas sensor is one of a lambda sensor and a temperature sensor;

wherein the spring element clamps at least two pressure bodies against the sensor element, the at least two pressure bodies being approximately diametrically opposed relative to the sensor element; and wherein the at least two pressure bodies are pressed together when the spring element is slid onto one of its axial ends and form a mouth open at its other axial end for accommodating the sensor element, and the mouth is closed by one of sliding the spring element in the direction of an axial end of the at least two pressure bodies and clamped on the sensor element by friction locking.

11. A gas sensor for monitoring a parameter of a gas component, the gas sensor comprising:

a sensor element;

at least one contact surface arranged on the sensor element;

at least one pressure body held against the sensor element by a spring element, wherein the spring element is annularly closed and is one of a clamping ring and a clamping sleeve that is shrunk onto the at least one pressure body; and a connecting line connected electrically to the at least one contact surface, wherein the connecting line is clamped by friction locking between the at least one contact surface and the at least one pressure body;

wherein the gas sensor is one of a lambda sensor and a temperature sensor;

wherein the spring element clamps at least two pressure bodies against the sensor element, the at least two pressure bodies being approximately diametrically opposed relative to the sensor element; and wherein the spring element on one of the axial ends of the at least two pressure bodies engages in a first notch surface on at least one of one of the ends and a second notch surface at one of the axial ends when pushed in a direction of the other axial end.

12. The gas sensor of claim 11, wherein the spring element is seated in the second notch surface at the other axial end of the at least two pressure bodies under increased spring tension.

13. The gas sensor of claim 11, wherein ramps are arranged between the first notch surface and the second notch surface for the spring element on the at least two pressure bodies spaced in an axial direction of the at least two pressure bodies so that the spring element is increasingly tensioned when pushed axially in a direction of the second notch surface.

14. The gas sensor of claim 11, wherein at least one of the first notch surface, the second notch surface, and ramps arranged between the first notch surface and the second notch surface is configured as a subregion of an axial channel on the at least two pressure bodies.

15. A gas sensor for monitoring a parameter of a gas component, the gas sensor comprising:
  a sensor element;
  at least one contact surface arranged on the sensor element;
  at least one pressure body held against the sensor element by a spring element, wherein the spring element is annularly closed and is one of a clamping ring and a clamping sleeve that is shrunk onto the at least one pressure body; and
  a connecting line connected electrically to the at least one contact surface, wherein the connecting line is clamped by friction locking between the at least one contact surface and the at least one pressure body;
  wherein the gas sensor is one of a lambda sensor and a temperature sensor; and
  wherein the spring element includes radially outward directed projections that anchor the spring element and parts clamped by the spring element to an inner wall of a housing part of the gas sensor by at least one of clamping and bracing via vibration damping.

16. A gas sensor for monitoring a parameter of a gas component, the gas sensor comprising:
  a sensor element;
  at least one contact surface arranged on the sensor element;
  at least one pressure body held against the sensor element by a spring element that includes at least one spring section, which, in a clamped state, is deformed in alignment with a component in parallel with a longitudinal axis of the sensor element; and
  a connecting line connected electrically to the at least one contact surface, the connecting line being clamped by friction locking between the contact surface and the at least one pressure body;
  wherein the gas sensor is one of a lambda sensor and a temperature sensor; and
  wherein the at least one spring section includes a tongue-like area directed radially inwardly.

* * * * *